United States Patent
Mineshima et al.

(10) Patent No.: US 7,722,561 B2
(45) Date of Patent: May 25, 2010

(54) PERITONEAL DIALYZER AND METHOD OF PERITONEAL DIALYSIS

(75) Inventors: Michio Mineshima, Tokyo (JP); Satoshi Suzuki, Tokyo (JP); Takashi Akiba, Tokyo (JP); Toshiaki Masuda, Osaka (JP); Susumu Kobayashi, Osaka (JP)

(73) Assignee: Nipro Corporation, Osaka (JP)

( * ) Notice: Subject to any disclaimer, the term of this patent is extended or adjusted under 35 U.S.C. 154(b) by 195 days.

(21) Appl. No.: 10/521,439

(22) PCT Filed: Jul. 15, 2003

(86) PCT No.: PCT/JP03/09000

§ 371 (c)(1), (2), (4) Date: Jan. 14, 2005

(87) PCT Pub. No.: WO2004/006992

PCT Pub. Date: Jan. 22, 2004

(65) Prior Publication Data

US 2005/0234392 A1 Oct. 20, 2005

(30) Foreign Application Priority Data

Jul. 17, 2002 (JP) .............................. 2002-208074

(51) Int. Cl.
*A61M 1/00* (2006.01)

(52) U.S. Cl. ....................................................... 604/29

(58) Field of Classification Search .................. 604/29, 604/30, 28, 27, 4.01, 5.01, 6.08, 65, 66, 67; 210/104, 645, 646

See application file for complete search history.

(56) References Cited

U.S. PATENT DOCUMENTS

| 4,190,047 | A | * | 2/1980 | Jacobsen et al. | ............... 604/28 |
|---|---|---|---|---|---|
| 4,618,343 | A | * | 10/1986 | Polaschegg | ................... 604/29 |
| 4,668,400 | A | * | 5/1987 | Veech | .......................... 210/647 |
| 4,976,683 | A | * | 12/1990 | Gauthier et al. | ................ 604/29 |
| 5,141,493 | A | * | 8/1992 | Jacobsen et al. | ............... 604/29 |
| 5,641,405 | A | | 6/1997 | Keshaviah et al. | .......... 210/645 |
| 5,783,072 | A | * | 7/1998 | Kenley et al. | ............ 210/195.2 |
| 6,280,634 | B1 | * | 8/2001 | Shah et al. | ................... 210/739 |
| 2002/0107474 | A1 | * | 8/2002 | Noack | ........................... 604/29 |
| 2003/0105424 | A1 | * | 6/2003 | Karoor et al. | .................. 604/29 |

FOREIGN PATENT DOCUMENTS

| EP | 0 980 685 A2 | 2/2000 |
|---|---|---|
| EP | 1 197 236 A2 | 4/2002 |

* cited by examiner

*Primary Examiner*—Nicholas D Lucchesi
*Assistant Examiner*—Christopher D Koharski
(74) *Attorney, Agent, or Firm*—Kubovcik & Kubovcik

(57) ABSTRACT

A peritoneal dialyzer including: a catheter capable of injecting and discharging peritoneal dialysate in an abdominal cavity of a patient; a peritoneal dialysate circuit connected to the catheter; and a dialyzer provided in the peritoneal dialysate circuit, the dialyzer including a hemodialysate circuit connected so that peritoneal dialysate passing through the inside can come into contact with a hemodialysate via a hollow fiber membrane, characterized in that means capable of measuring an osmotic agent concentration in the peritoneal dialysate is provided on the peritoneal dialysate circuit on the side of the end at which the catheter is connected with respect to the dialyzer, and a mechanism for dehydrating the peritoneal dialysate according to the osmotic agent concentration measured by the aforementioned means is provided on the hemodialysate circuit, and a method of peritoneal dialysis using the peritoneal dialyzer.

9 Claims, 2 Drawing Sheets

PERITONEAL DIALYZER AND METHOD OF PERITONEAL DIALYSIS

This application is a 371 of international application PCT/JP2003/009000, which claims priority based on Japanese patent application No. 2002208074 filed Jul. 17, 2002, which is incorporated herein by reference.

TECHNICAL FIELD

The present invention relates to a peritoneal dialyzer for removing waste products or water contained in the blood of a patient by injecting and discharging peritoneal dialysate into/from an abdominal cavity of the patient using a catheter or the like and a method thereof. More specifically, the invention relates to a peritoneal dialyzer used for a method of peritoneal dialysis which transports part of the dialysate stored in the abdominal cavity of the patient outside the body, removes unnecessary substances from the peritoneal dialysate positively by an external dialyzer, and returns the peritoneal dialysate into the abdominal cavity again (CRPD: Continuous Recirculation Peritoneal Dialysis or BPD: Bi-directional Peritoneal Dialysis) and a method thereof.

RELATED ART

A kidney of a mammal behaves to maintain acid-base and electrolyte balance constantly and to remove undesirable substances generated by metabolism in the body from blood as a normal function. In the past, hemodialysis, peritoneal dialysis or the like has been conducted for a patient whose kidney is depressed in function. In hemodialysis, blood taken out from the patient is injected into an external dialyzer, and the blood is brought into contact with one side of a selectively permeable membrane in the dialyzer, for example, a hollow fiber membrane manufactured from acetylcellulose, and hemodialysate is brought into contact with the opposite side thereof. Based on the principle of diffusion, waste products in the blood are transferred through the aforementioned membrane into the hemodialysate, and water is removed by ultrafiltration. This treatment is normally used in the outpatient department of a hospital, and there is a problem that the patient is restricted to the hospital for a long time.

On the other hand, peritoneal dialysis is a well-established alternative method to extracorporeal hemodialysis and has advantages in that the patient is not restricted to the hospital for a long time, and it can be conducted at home. Also, peritoneal dialysis is an effective method of treatment for a patient who has difficulty receiving extracorporeal hemodialysis. In peritoneal dialysis, peritoneal dialysate, which is fresh and contains a large amount of glucose, is injected into the abdominal cavity of the patient, is stored for a few hours to allow waste products and water in the patient's blood to be transferred through the peritoneum as the selectively permeable membrane into the peritoneal dialysate, and then the peritoneal dialysate containing the waste products is discharged from the abdominal cavity. However, this method has problems such that it may cause peritoneal sclerosis, the treatment takes a long time since dialyzing efficiency is lower than hemodialysis, and peritoneal dialysate on the market is expensive.

Therefore, a number of improved peritoneal dialysis methods for increasing dialyzing efficiency and thus reducing the time required for the treatment and cost required for the treatment are known.

For example, in the specification of U.S. Pat. No. 5,141,493, a system in which an abdominal cavity of a patient and a peritoneal dialysate purifying circuit are connected by a line having a reversible pump disposed therein for continuously purifying the peritoneal dialysate is disclosed, and peritoneal dialysate transferred from the abdominal cavity of the patient is purified by an external dialyzer disposed in the peritoneal dialysis purifying circuit and is returned into the abdominal cavity again. Also, Japanese patent Laid-open No. 9-501862 discloses a system in which an abdominal cavity of a patient and a liquid bag are connected by a line having a reversible pump disposed therein, and peritoneal dialysate transferred from the abdominal cavity of the patient is passed through a dialyzer (for example, a hollow fiber membrane type purifier), is temporarily stored in a liquid bag, and is returned again through the dialyzer into the abdominal cavity.

The peritoneal dialysate used in the peritoneal dialyzer shown in the two examples described above employs glucose as the osmotic agent, and dehydration is performed between blood flowing in peritoneal capillary blood vessels by osmotic pressure of glucose and the peritoneal dialysate. However, there is a problem that it is necessary to replenish the glucose using a glucose inspirator or the like during dialysis in order to maintain the osmotic pressure (dehydrating capability) of the peritoneal dialysate because glucose (molecular weight of 180) passes through the hollow fiber membrane when purifying the peritoneal dialysate by the external dialyzer and almost 100% is taken out of the peritoneal dialysate.

On the other hand, a method of peritoneal dialysis using peritoneal dialysate containing an osmotic agent which does not pass through the hollow fiber membrane of the dialyzer when being purified by the external dialyzer has also been developed (JP-A-2000-72658), in which albumin (molecular weight of about 69,000), glucose polymer, dextran, and the like are exemplified as the osmotic agent. With peritoneal dialysate as described above, there is no possibility that osmotic agent of the peritoneal dialysate is removed when being purified by the external dialyzer.

However, in such peritoneal dialysate, since the penetrating agent concentration in the peritoneal dialysate is lowered by transferring water in the patient's blood to the peritoneal dialysate, it is necessary to replenish the osmotic agent as needed, or to replace the peritoneal dialysate with a new one. It is because the peritoneal dialysate with reduced penetrating agent concentration is lowered in osmotic pressure, and dialyzing efficiency and dehydrating efficiency is not good in peritoneal dialysis, whereby it is difficult to reuse the same. However, since the osmotic agent is expensive, replenishment of the osmotic agent and replacement of peritoneal dialysate containing the osmotic agent increases the cost for dialysis treatment.

In view of such circumstances, it is an object of the present invention to provide a peritoneal dialyzer which can reduce the time for dialysis treatment and treatment cost by increasing dialyzing efficiency and dehydrating efficiency, and a method of using the same.

DISCLOSURE OF THE INVENTION

After having conducted an intensive study to solve the problem described above, the present inventors have found that the above-described problems can be solved by using a peritoneal dialysate containing an osmotic agent which cannot pass through a hollow fiber membrane of a dialyzer, measuring the osmotic agent concentration in the peritoneal dialysate as needed and removing a required amount of water from the peritoneal dialysate by an external dialyzer so that the osmotic agent concentration is adjusted to a predetermined concentration, and achieved the present invention.

In other words, the present invention is a peritoneal dialyzer including a catheter capable of injecting and discharging peritoneal dialysate into/from an abdominal cavity of a patient, a peritoneal dialysate circuit connected to the catheter, and a dialyzer provided in the peritoneal dialysate circuit, the dialyzer including a hemodialysate circuit connected so that peritoneal dialysate passing through the inside can come into contact with hemodialysate via a hollow fiber membrane, characterized in that means capable of measuring the osmotic agent concentration in the peritoneal dialysate is provided in the peritoneal dialysate circuit on the side of the end at which the catheter is connected with respect to the dialyzer, and a mechanism for dehydrating the peritoneal dialysate according to the osmotic agent concentration measured by the aforementioned means is provided in the hemodialysate circuit.

Also, the present invention is a peritoneal dialysis method using the peritoneal dialyzer including a catheter capable of injecting and discharging peritoneal dialysate in an abdominal cavity of a patient, a peritoneal dialysate circuit connected to the catheter, and a dialyzer provided in the peritoneal dialysate circuit, the dialyzer including a hemodialysate circuit connected so that peritoneal dialysate passing through the inside can come into contact with hemodialysate via a hollow fiber membrane, which method includes (a) taking peritoneal dialysate out from a patient and measuring the osmotic agent concentration (c1) in the peritoneal dialysate;

(b) calculating the amount of dehydration (uf1) of the peritoneal dialysate required for adjusting the osmotic agent concentration (c1) in the peritoneal dialysate to a predetermined osmotic agent concentration (c2), (c) removing water corresponding to the calculated amount of dehydration (uf1) of the peritoneal dialysate via the dialyzer; and (d) injecting the peritoneal dialysate into the patient again.

Preferred embodiments of a peritoneal dialyzer of the present invention shown in the attached drawings will be described in detail below, but the present invention is not limited to the description.

BEST MODE FOR CARRYING OUT THE INVENTION

Figure 1:
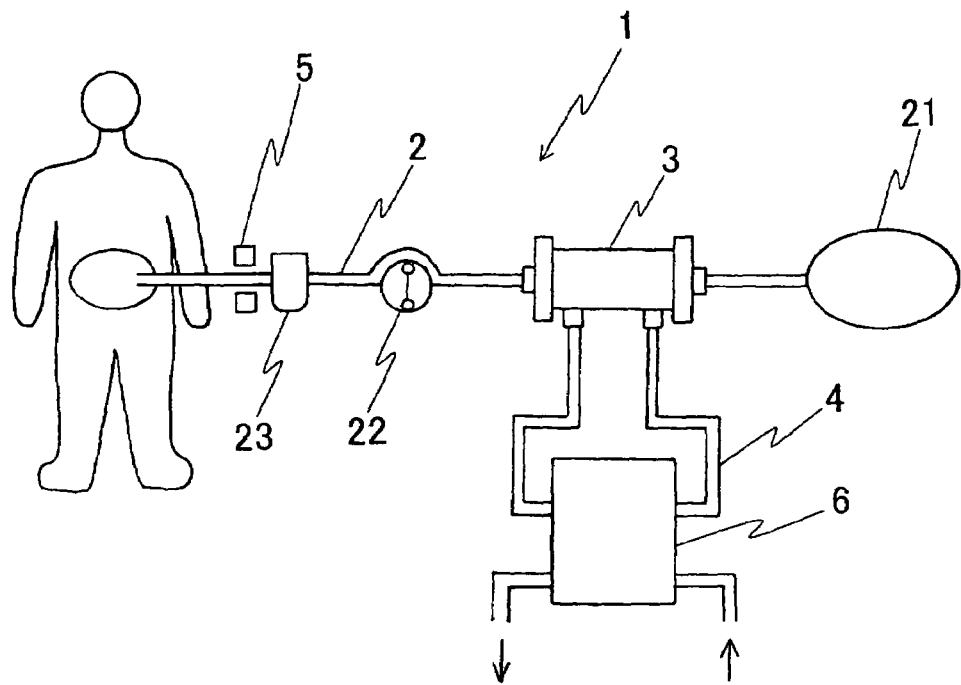
FIG. 1 is a flow diagram showing a first embodiment of a peritoneal dialyzer according to the present invention.

As shown in FIG. 1, a peritoneal dialyzer 1 according to the present invention includes a catheter (not shown) to be indwelled in a patient, a peritoneal dialysate circuit 2 to be connected to the catheter, a dialyzer 3 provided in the peritoneal dialysate circuit 2, and a hemodialysate circuit 4 to be connected to the dialyzer 3.

The peritoneal dialysate circuit 2 to be connected to the catheter is, for example, a tube formed of flexible resin such as vinyl chloride or a polyolefin, and must be superior in safety as a matter of course, transparency and anti-kinking property. The total length of the peritoneal dialysate circuit 2 is 10 to 300 cm, and preferably, 100 to 250 cm. If the total length is longer than 300 cm, peritoneal dialysate remains in the circuit 2, and the amount of peritoneal dialysate to be injected into the abdominal cavity may be reduced, which is not preferable. Such a tube is fabricated by a known method such as extrusion molding.

The dialyzer 3 is provided in the aforementioned peritoneal dialysate circuit 2. The dialyzer 3 includes a number of hollow fiber membranes in a bundle loaded therein, and a casing for timely inflowing and outflowing peritoneal dialysate. The bundle of the hollow fiber membranes is supported at the end with a diaphragm member which is formed of a synthetic polymer substance fixed at the end of the casing. The opening of the respective hollow membrane is opened to the outer end surface of the diaphragm wall member.

The casing is additionally provided with an inflow port and an outflow port for hemodialysate, to which the hemodialysate circuit 4 is connected. With the dialyzer 3, peritoneal dialysate is flowed inside the hollow fiber membrane and hemodialysate is flowed outside the same to bring the peritoneal dialysate and the hemodialysate into contact with each other via the membrane for performing dialysis, and waste products in the dialysate are removed. By purifying the peritoneal dialysate, continuous peritoneal dialysis reusing the peritoneal dialysate is enabled.

The hollow fiber membrane is a hollow fiber formed of, for example, a cellulosic membrane (acetylcellulose, cuprophan, and so on), a synthetic polymer membrane (polyacrylonitrile, polymethyl methacrylate, ethylene-vinyl alcohol, polysulphone, polyamide, and so on) or the like, and preferably is capable of filtering out substances having a molecular weight of about 2000 to 7000, more preferably, 5,000 to 10,000. With such a hollow fiber membrane, peritoneal dialysate can be prevented from being invaded by bacteria through the hollow fiber membrane even when bacteria enter in the hemodialysate.

Peritoneal dialysate used in the present invention preferably contains an osmotic agent which does not pass through the aforementioned hollow fiber membrane. Such an osmotic agent is preferably at least one compound selected from a group including albumin, glucose polymer and dextran, and is specifically preferably albumin.

The molecular weight of the albumin is normally about 69,000. Albumin is preferably human serum albumin, and may be genetically-engineered. The albumin concentration in the peritoneal dialysate is preferably 20 to 250 g/L, and specifically preferably 70 to 150 g/L, which is the same range as that of the osmotic pressure (including colloidal osmotic pressure) for peritoneal dialysate using glucose which has been generally used so far. If the content of albumin is smaller than 20 g/L, dehydrating capability is not sufficient, and if it exceeds 250 g/L, osmotic pressure is too high and not preferable for the patient. The peritoneal dialysate may contain N-acetyltryptophan or sodium caprylate as an albumin stabilizing agent. As glucose polymer, one having a molecular weight of 30,000 to 80,000, for example, dextran partial hydrolytic substances having a molecular weight of about 75,000, is preferable.

In addition to the osmotic agent, the aforementioned peritoneal dialysate includes a physiologically acceptable electrolyte, a pH adjuster or the like, and is adjusted to a solution having a total osmotic pressure of about 200 to about 600 mOsm/L, more preferably, about 270 to about 500 mOs/L.

Such peritoneal dialysate may have a composition, for example, as follows.

| | |
|---|---|
| albumin (g/L) | about 20 to about 250 |
| sodium ion (mEq/L) | about 130 to about 140 |
| calcium ion (mEq/L) | about 3.0 to about 4.5 |
| magnesium ion (mEq/L) | about 0.5 to about 2.0 |
| chlorine ion (mEq/L) | about 95 to about 110 |
| lactate ion (mEq/L) | about 35 to about 40 |

Hemodialysate used in the present invention is one used in normal hemodialysis. Since the hemodialysate adjusting agent is provided in a state of a powder or in a state of a high concentration liquid, it is mixed with RO (reverse osmotic) water for adjusting as a hemodialysate having a predetermined concentration and is supplied to the dialyzer 3.

Such hemodialysate contains, for example, the following contents.

| | |
|---|---|
| sodium (mEq/L) | about 130 to about 145 |
| potassium (mEq/L) | about 2.0 to about 2.5 |
| calsium (mEq/L) | about 2.5 to about 4.0 |
| magnesium (mEq/L) | about 1.0 to about 1.5 |
| chloro (mEq/L) | about 95 to about 115 |
| sodium bicarbonate (mEq/L) | about 25 to about 30 |
| glucose (g/L) | about 90 to about 500 |

The peritoneal dialyzer 1 according to the present invention additionally includes means 5 which is capable of measuring the concentration of osmotic agent. The means 5 measures the concentration of osmotic agent contained in peritoneal dialysate flowing in the peritoneal dialysis circuit 2, and is preferably provided in the vicinity of the connecting end of the catheter in the peritoneal dialysate circuit 2. As detailed examples of this means, an ultrasonic wave measuring apparatus, a refractive index measuring instrument, a light absorption instrument and a conductive rate measuring instrument are used, and two or more of these may be used, if necessary.

The hemodialysate circuit 4 constituting the peritoneal dialyzer 1 according to the present invention is further provided with a dehydrating mechanism 6. This is for dehydrating the peritoneal dialysate as needed so that the concentration of osmotic agent measured by the aforementioned osmotic agent concentration measuring means 5 is adjusted to a predetermined concentration. Since the osmotic agent contained in the peritoneal dialysate is expensive, it is necessary to prevent it from being removed from the peritoneal dialysate as much as possible. Therefore, in the present invention, a peritoneal dialysate using an osmotic agent which cannot pass through the hollow fiber membrane in the dialyzer 3 is employed, and the mechanism 6 which dehydrates the peritoneal dialysate via the dialyzer 3 is provided. Dehydration of the peritoneal dialysate via the dialyzer 3 is performed by a pump provided in the hemodialysate circuit 4.

Figure 3:
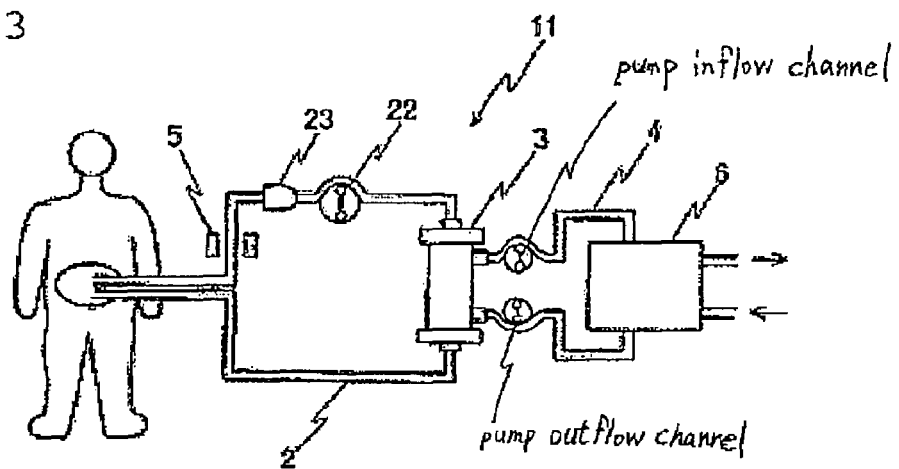
FIGS. 3-5 show embodiments of a peritoneal dialyzer according to the present invention using different mechanisms for dehydrating the peritoneal dialysate.

As an example of such a dehydrating mechanism 6, there is shown in FIG. 3 a mechanism which performs dehydration by providing pumps in a hemodialysate inflow channel to the dialyzer 3 and a hemodialysate outflow channel from the dialyzer 3 respectively, and by driving the same so that a flux in the pump on the outflow channel side is larger than a flux in the pump on the inflow channel side.

Figure 4:
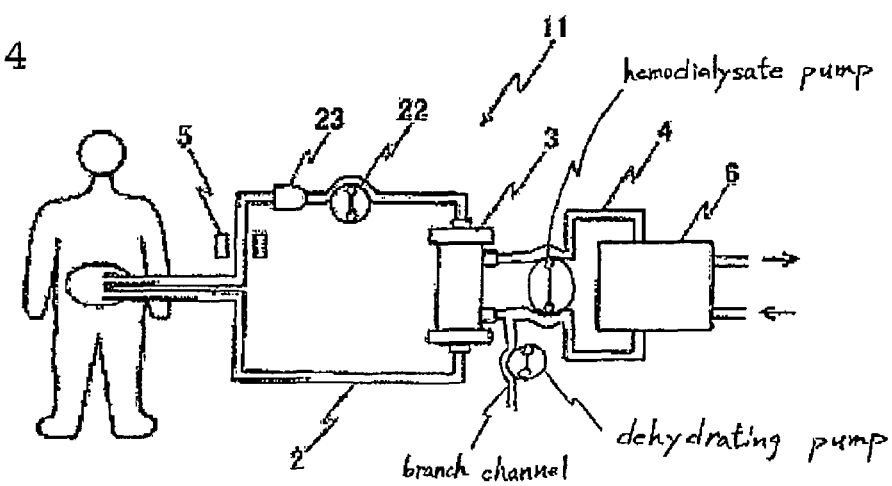

As another dehydrating mechanism 6, there is shown in FIG. 4 a mechanism which performs dehydration by arranging a pump which can equalize the flux of hemodialysate inflowing into the dialyzer 3 and the flux of hemodialysate outflowing from the dialyzer 3, for example, a balance chanter or a dual pump, in the hemodialysate circuit 4; providing a branch channel on the hemodialysate outflow channel at a position closer to the dialyzer 3 than the pump; and driving a dehydrating pump provided in the branch channel so that the amount of hemodialysate outflowing from the dialyzer 3 becomes larger than the amount of hemodialysate inflowing into the dialyzer 3.

Figure 5:
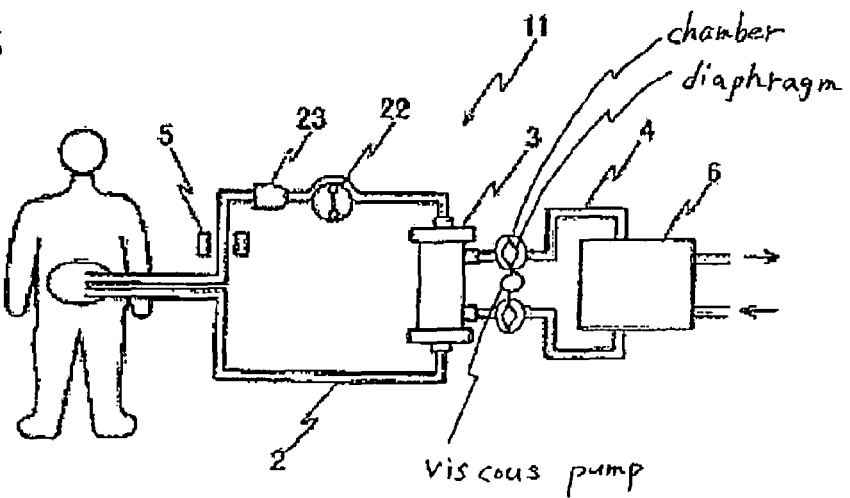

As still another dehydrating mechanism 6, there is shown in FIG. 5 a mechanism (Japanese Patent No. 1692872) in which a viscous pump which can vary the capacities of a chamber on the side of the hemodialysate inflow channel and a chamber on the side of the hemodialysate outflow channel according to the movement of a diaphragm is provided, and dehydration is performed by varying the capacities so that the capacity of the chamber on the side of the inflow channel is smaller than the capacity off the chamber on the side of the outflow channel and the amount of hemodialysate outflowing from the dialyzer 3 is larger than the amount of hemodialysate inflowing into the dialyzer 3.

At the end of the peritoneal dialysate circuit 2 used in the present invention opposite from the end which is connected to the catheter, a peritoneal dialysate source 21 may be provided as shown in FIG. 1. The peritoneal dialysate source 21 is for temporarily storing peritoneal dialysate to be injected into the abdominal cavity of the patient and peritoneal dialysate discharged from the abdominal cavity of the patient during the treatment of peritoneal dialysis. Although the shape and material are not specifically limited, for example, a soft bag formed of vinyl chloride, polyolefin resin or the like is used.

Figure 2:
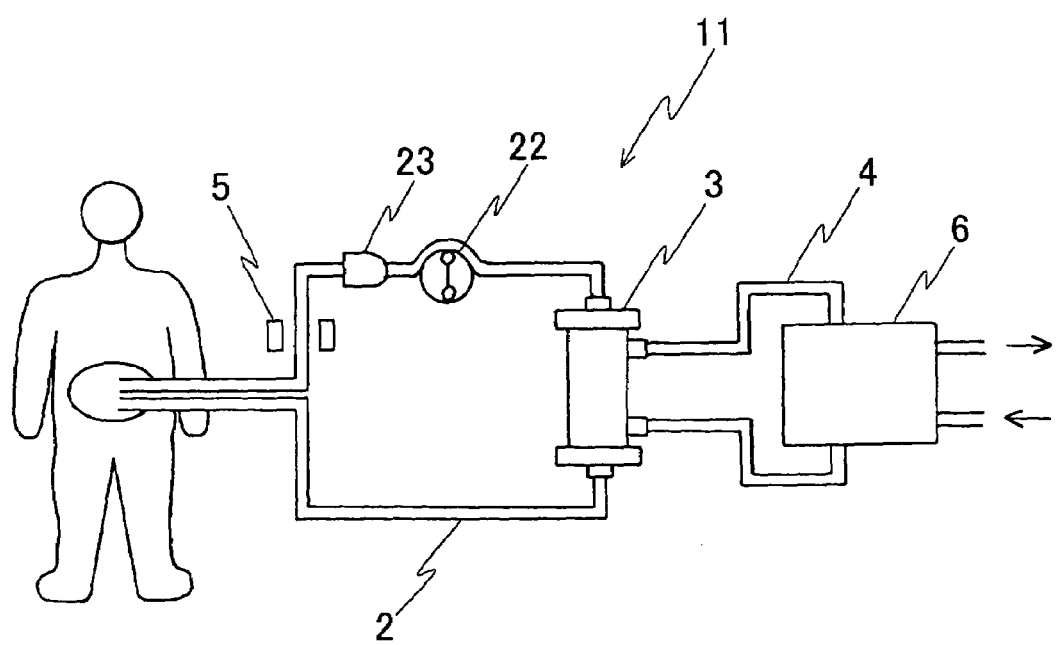
FIG. 2 is a flow diagram showing a second embodiment of the peritoneal dialyzer according to the present invention.

Instead of providing the aforementioned peritoneal dialysate source 21, it is also possible to employ a double-lumen catheter instead of the single-lumen catheter shown in FIG. 1, to connect two peritoneal dialysate circuits 2 which can communicate with the respective lumens at the end of the catheter, and form a closed circuit by connecting the two circuits 2 with the dialyzer 4 as shown in FIG. 2. In the peritoneal dialyzer 11 of such a structure, since injection and discharge of peritoneal dialysate into/from the abdominal cavity of the patient can be performed simultaneously, it is preferable in that the concentration of osmotic agent in the peritoneal dialysate in the abdominal cavity can be gradually varied.

It is also possible to provide a pump 22 on the peritoneal dialysate circuit 2. When peritoneal dialysate is injected into the abdominal cavity of the patient, there is a case where it is injected naturally by a difference in gravity by hanging the peritoneal dialysate source 21 at a level higher than the abdominal cavity of the patient. Also, when discharging the peritoneal dialysate from the abdominal cavity of the patient, there is a case where it is discharged naturally by a difference in gravity by disposing the peritoneal dialysate source 21 at a level lower than the abdominal cavity of the patient. However, by providing the pump 22 on the circuit 2, discharge and injection of peritoneal dialysate at a predetermined velocity is achieved without performing a specific manual operation, such as arrangement of the peritoneal dialysate source 21. The pump used in this case may be a chamber-type pump which pressurizes or depressurizes the peritoneal dialysate source 21 directly as well as a roller pump or a finger pump.

In addition, it is also possible to provide other components which are required for performing peritoneal dialysis such as a drip chamber 23 and pressure measuring means in the peritoneal dialysate circuit 2 and a warmer, concentration measuring means and a flow meter in the hemodialysate circuit 4 in the peritoneal dialyzer 1 of the present invention.

Preferably, the osmotic agent concentration measuring means 5 and the dehydration mechanism 6 according to the present invention can be worked in association with each other. For example, it is preferable to provide control means (not shown) which calculates the difference between the concentration (c1) measured by the osmotic agent concentration measuring means 5 and the predetermined osmotic agent concentration (c2), calculates the amount of dehydration (uf1) of peritoneal dialysate required for eliminating the difference in concentration, and controls the dehydration mechanism 6 for dehydrating the peritoneal dialysate by the amount of the dehydration (uf1).

The aforementioned predetermined osmotic agent concentration (c2) is predetermined by a dehydration program or the like specific for the patient, which is stored in the control means. In general, the osmotic agent concentration (c2) is set to a high value immediately after initiating the peritoneal dialysis because the amount of water that must be transferred from the patient's body into the peritoneal dialysate is large. However, the osmotic agent concentration (c2) is set to a low value as the peritoneal dialysis proceeds because the amount of water in the patient's body is decreasing and the amount of water that must be transferred into the peritoneal dialysate decreases.

The aforementioned dehydration program is set as needed depending on the period of time for performing dialysis, in addition to the weight, the height, the sex, and water permeability of the peritoneum of the patient. However, even when the dialysis conditions have changed due to the influence of a change in the patient's physical condition, the peritoneal dialyzer 1 of the present invention can adjust the concentration of osmotic agent in the peritoneal dialysate by varying the osmotic agent concentration (c2) and changing the amount of dehydration from the patient's blood. Also, it is possible to know the condition of the patient on that day from the osmotic agent concentration (c1) measured by the osmotic agent concentration measuring means 5, and it is possible to perform peritoneal dialysis more suitable for the patient by changing the dehydration program to match the conditions.

Subsequently, referring to FIG. 1, a method of peritoneal dialysis using the peritoneal dialyzer of the present invention will be described.

In a first place, the peritoneal dialyzer 1 is set to a catheter indwelled in the abdominal cavity of the patient by known means. The pump 22 is rotated in the normal direction only when peritoneal dialysate is already stored in the abdominal cavity of the patient to discharge the peritoneal dialysate from the abdominal cavity of the patient. At this time, the osmotic agent concentration (c1) in the peritoneal dialysate is measured by the osmotic agent concentration measuring means 5.

The concentrations of the respective components in the peritoneal dialysate are adjusted by being brought into contact with hemodialysate via the hollow fiber membrane and by being dialyzed when passing through the dialyzer 3. The aforementioned osmotic agent concentration (c1) is compared with the predetermined osmotic agent concentration (c2) by the control means (not shown), and the amount of dehydration (uf1) from the peritoneal dialysate required for adjusting the osmotic agent concentration (c1) in the peritoneal dialysate to the concentration (c2) is calculated. The dehydration mechanism 6 is driven for dehydrating the peritoneal dialysate by the amount of dehydration (uf1), and water in the peritoneal dialysate is transferred to the hemodialysate via the hollow fiber membrane of the dialyzer 3.

The peritoneal dialysate which is dialyzed and dehydrated is temporarily stored in the peritoneal dialysate source 21. When discharge of the specified amount of peritoneal dialysate from the patient has been completed, the pump 22 is rotated in the reverse direction, so that the peritoneal dialysate stored in the peritoneal dialysate source 21 is injected again into the patient's body. At this time, the peritoneal dialysate may be dialyzed and/or dehydrated when passing through the dialyzer 3 again.

INDUSTRIAL APPLICABILITY

The peritoneal dialyzer of the present invention measures the osmotic agent concentration c1 in the peritoneal dialysate and dehydrates the peritoneal dialysate by a required amount for adjusting the osmotic agent concentration (c1) in the peritoneal dialysate to the predetermined osmotic agent concentration (c2). Therefore, since the dialyzing efficiency and the dehydrating efficiency of the peritoneal dialysate are not deteriorated, the peritoneal dialysate can be repeatedly used. Also, in the present invention, since the osmotic agent in the peritoneal dialysate is prevented from being discharged out of the peritoneal dialysate by dehydrating the peritoneal dialysate via a dialyzer, additional replenishment of expensive osmotic agent is not necessary and there is no fear of increasing the treatment cost. In addition, according to the peritoneal dialyzer of the present invention, peritoneal dialysis can be performed under dialyzing conditions suitable for the patient because a peritoneal dialysate having an osmotic agent concentration suitable for the conditions of the patient can be injected into the patient as needed by changing the predetermined osmotic agent concentration (c2) in the peritoneal dialysate.

The invention claimed is:

1. A peritoneal dialyzer comprising: a catheter capable of injecting and discharging peritoneal dialysate in an abdominal cavity of a patient; a peritoneal dialysate circuit external of the patient connected to the catheter; and a dialyzer provided in the peritoneal dialysate circuit, said dialyzer comprising a hemodialysate circuit connected so that peritoneal dialysate passing through the inside contacts hemodialysate via a hollow fiber membrane, wherein a means for measuring an osmotic agent concentration in peritoneal dialysate flowing in the peritoneal dialysate circuit is provided in the peritoneal dialysate circuit on the side of the end at which the catheter is connected with respect to the dialyzer, and a mechanism for dehydrating the peritoneal dialysate according to the osmotic agent concentration measured by said means is provided in the hemodialysate circuit, and the peritoneal dialysate in the peritoneal dialysate circuit contacts the hemodialysate in the hemodialysate circuit via the membrane of said dialyzer and water in the peritoneal dialysate is removed to the hemodialysate via said dialyzer by said dehydrating mechanism, said dehydrating mechanism being one selected from the group consisting of:

(1) a pump provided in a hemodialysate inflow channel to the dialyzer and a pump provided in a hemodialysate outflow channel from the dialyzer, the pumps being driven so that a flux in the pump on the outflow channel side is larger than a flux in the pump on the inflow channel side;

(2) a pump which can equalize the flux of hemodialysate inflowing into the dialyzer and the flux of hemodialysate outflowing from the dialyzer arranged in the hemodialysate circuit; a branch channel provided on a hemodialysate outflow channel at a position closer to the dialyzer than said pump; and a dehydrating pump provided in the branch channel and driven so that the amount of hemodialysate outflowing from the dialyzer becomes larger than the amount of hemodialysate inflowing into the dialyzer; and (3) a viscous pump which varies the capacities of a chamber on the side of the hemodialysate inflow channel and a chamber on the side of the hemodialysate outflow channel according to the movement of a diaphragm provided in the hemodialysate circuit, with dehydration being performed by varying the capacities so that the capacity of the chamber on the side of the inflow channel is smaller than the capacity of the chamber on the side of the outflow channel and the amount of hemodialysate outflowing from the dialyzer is larger than the amount of hemodialysate inflowing into the dialyzer.

2. A peritoneal dialyzer according to claim 1, characterized in that said means for measuring said osmotic agent concentration is at least one type of means selected from the group consisting of an ultrasonic wave measuring apparatus, a refractive index measuring instrument, a light absorption instrument, and a conductive rate measuring instrument.

3. A peritoneal dialyzer according to claim 1, characterized in that osmotic agent cannot pass through a hollow fiber membrane in the dialyzer.

4. A peritoneal dialyzer according to claim 1, characterized in that said osmotic agent is at least one type of compound selected from the group consisting of albumin, glucose polymer and dextran.

5. A method of peritoneal dialysis using a peritoneal dialyzer comprising a catheter capable of injecting and discharging peritoneal dialysate into/from an abdominal cavity of a patient, a peritoneal dialysate circuit external of the patient connected to the catheter, and a dialyzer provided in the peritoneal dialysate circuit, said dialyzer including a hemodialysate circuit connected so that peritoneal dialysate passing through the inside can come into contact with hemodialysate via a hollow fiber membrane, and which includes (a) taking peritoneal dialysate out from a patient and measuring an osmotic agent concentration ($c_1$) in the peritoneal dialysate;

(b) calculating an amount of dehydration ($uf_1$) of the peritoneal dialysate required for adjusting the osmotic agent concentration ($c_1$) in the peritoneal dialysate to a predetermined osmotic agent concentration ($c_2$), (c) removing water corresponding to the calculated amount of dehydration ($uf_1$) in the peritoneal dialysate via said dialyzer by a dehydrating mechanism in which the peritoneal dialysate in the peritoneal dialysate circuit contacts the hemodialysate in the hemodialysate circuit via the membrane of said dialyzer and water in the peritoneal dialysate is removed to the hemodialysate via said dialyzer; and (d) injecting the peritoneal dialysate into the patient again; wherein said dehydrating mechanism is one in which an amount of hemodialysate outflowing from the dialyzer is made to be larger than an amount of hemodialysate inflowing into the dialyzer.

6. A method of peritoneal dialysis according to claim 5, characterized in that measurement of the osmotic agent concentration in said peritoneal dialysate is performed by at least one type of means selected from the group consisting of an ultrasonic wave measuring apparatus, a refractive index measuring instrument, a light absorption instrument, and a conductive rate measuring instrument, provided in the peritoneal dialysate circuit on the side of the end at which the catheter is connected with respect to the dialyzer.

7. A method of peritoneal dialysis according to claim 5, characterized in that the amount of hemodialysate outflowing from the dialyzer is made to be larger than an amount of hemodialysate inflowing into the dialyzer by a pump provided on the hemodialysate circuit.

8. A peritoneal dialyzer according to according to claim 1, characterized in that said osmotic agent cannot pass through the hollow fiber membrane in the dialyzer.

9. A peritoneal dialyzer according to claim 1, characterized in that said osmotic agent is at least one type of compound selected from the group consisting of albumin, glucose polymer and dextran.

* * * * *